United States Patent
Dalgleish et al.

(10) Patent No.: US 10,478,590 B2
(45) Date of Patent: *Nov. 19, 2019

(54) SLEEP ASSISTANCE DEVICE FOR MULTIPLE USERS

(71) Applicant: Bose Corporation, Framingham, MA (US)

(72) Inventors: Martin James Dalgleish, Glasgow (GB); Brian David Mulcahey, Sudbury, MA (US)

(73) Assignee: Bose Corporation, Framingham, MA (US)

( * ) Notice: Subject to any disclaimer, the term of this patent is extended or adjusted under 35 U.S.C. 154(b) by 70 days.

This patent is subject to a terminal disclaimer.

(21) Appl. No.: 15/655,836

(22) Filed: Jul. 20, 2017

(65) Prior Publication Data
US 2018/0078735 A1    Mar. 22, 2018

Related U.S. Application Data

(63) Continuation-in-part of application No. 15/267,567, filed on Sep. 16, 2016.

(51) Int. Cl.
*A61M 21/02* (2006.01)
*A61B 5/00* (2006.01)
(Continued)

(52) U.S. Cl.
CPC .......... *A61M 21/02* (2013.01); *A61B 5/4812* (2013.01); *A61B 5/6898* (2013.01); *G06F 3/165* (2013.01);
(Continued)

(58) Field of Classification Search
CPC ....... A61B 5/746; A61B 5/024; A61B 5/4836; A61B 5/4812; A61B 5/11; A61B 5/0816;
(Continued)

(56) References Cited

U.S. PATENT DOCUMENTS 4,228,806 A   10/1980 Lidow
5,781,640 A   7/1998 Nicolino, Jr.
(Continued)

FOREIGN PATENT DOCUMENTS

CN    105231997 A    1/2016
EP    2278507 A2     1/2011
(Continued)

OTHER PUBLICATIONS

International Search Report and Written Opinion for application No. PCT/US2017/051575 dated Dec. 1, 2017.
(Continued)

*Primary Examiner* — Navin Natnithithadha
*Assistant Examiner* — Sunita Reddy
(74) *Attorney, Agent, or Firm* — Bose Corporation

(57) ABSTRACT

A sleep assistance device is provided-for, including a contactless biometric sensor, a processor, memory, and a speaker. The processor detects a user's sleep state by reading signals from the contactless biometric sensor. The processor may then initiate a wind-down routine upon detecting a sleep-readiness state, including playing relaxing sounds or playing a respiration entrainment sound. The processor may also play noise-masking sounds upon detecting that a user has fallen asleep and seamlessly transition between the sounds played during the wind-down routine and the noise-masking sounds.

6 Claims, 9 Drawing Sheets

(51) Int. Cl.
*G06F 3/16* (2006.01)
*A61M 21/00* (2006.01)
*G10L 15/22* (2006.01)
*H04R 1/04* (2006.01)
*H04R 1/02* (2006.01)
*H04R 1/32* (2006.01)
*H04R 29/00* (2006.01)
*A61B 5/024* (2006.01)
*A61B 5/08* (2006.01)
*A61B 5/11* (2006.01)

(52) U.S. Cl.
CPC .............. *A61B 5/024* (2013.01); *A61B 5/0816* (2013.01); *A61B 5/11* (2013.01); *A61B 5/4836* (2013.01); *A61B 2560/0242* (2013.01); *A61M 2021/0027* (2013.01); *A61M 2021/0083* (2013.01); *A61M 2021/0088* (2013.01); *A61M 2205/3303* (2013.01); *A61M 2205/3306* (2013.01); *A61M 2205/3368* (2013.01); *A61M 2205/3375* (2013.01); *A61M 2205/3553* (2013.01); *A61M 2205/3561* (2013.01); *A61M 2205/3569* (2013.01); *A61M 2205/3584* (2013.01); *A61M 2205/3592* (2013.01); *A61M 2205/502* (2013.01); *A61M 2205/505* (2013.01); *A61M 2205/52* (2013.01); *A61M 2205/581* (2013.01); *A61M 2205/583* (2013.01); *A61M 2205/80* (2013.01); *A61M 2230/06* (2013.01); *A61M 2230/42* (2013.01); *A61M 2230/63* (2013.01); *G10L 15/22* (2013.01); *G10L 2015/223* (2013.01); *H04R 1/028* (2013.01); *H04R 1/04* (2013.01); *H04R 1/326* (2013.01); *H04R 29/00* (2013.01); *H04R 2420/07* (2013.01)

(58) Field of Classification Search
CPC ......... A61B 2560/0242; A61B 5/6898; A61M 2230/42; A61M 2230/06; A61M 2205/80; A61M 2205/583; A61M 2205/581; A61M 2205/3584; A61M 2021/0088; A61M 2021/0027; A61M 21/02; A61M 2205/505; A61M 2230/63; A61M 2021/0083; A61M 2205/3303; A61M 2205/3306; A61M 2205/3368; A61M 2205/3375; A61M 2205/3553; A61M 2205/3561; A61M 2205/3569; A61M 2205/3592; A61M 2205/502; A61M 2205/52; A61M 2230/005; G06F 17/30764
USPC ................. 128/897–899; 600/26–28
See application file for complete search history.

(56) References Cited

U.S. PATENT DOCUMENTS

| | | |
|---|---|---|
| 5,928,133 A | 7/1999 | Halyak |
| 6,236,622 B1 | 5/2001 | Blackman |
| 6,662,032 B1 | 12/2003 | Gavish et al. |
| 6,825,769 B2 | 11/2004 | Colmenarez et al. |
| 6,888,779 B2 | 5/2005 | Mollicone et al. |
| 7,248,915 B2 | 7/2007 | Ronnholm |
| 7,637,859 B2 | 12/2009 | Lindback et al. |
| 7,850,619 B2 | 12/2010 | Gavish et al. |
| 8,243,937 B2 | 8/2012 | Nicolino, Jr. et al. |
| 8,280,067 B2 | 10/2012 | Nicolino, Jr. et al. |
| 8,280,068 B2 | 10/2012 | Nicolino, Jr. et al. |
| 8,285,344 B2 | 10/2012 | Kahn et al. |
| 8,379,870 B2 | 2/2013 | Nicolino, Jr. et al. |
| 8,485,982 B2 | 7/2013 | Gavish et al. |
| 8,550,978 B2 | 10/2013 | Ullmann |
| 8,562,526 B2 | 10/2013 | Heneghan et al. |
| 8,585,607 B2 | 11/2013 | Klap et al. |
| 8,731,646 B2 | 5/2014 | Halperin et al. |
| 8,855,334 B1 | 10/2014 | Lavine et al. |
| 8,870,764 B2 | 10/2014 | Rubin |
| 8,870,785 B2 | 10/2014 | Muehlsteff et al. |
| 8,941,431 B2 | 1/2015 | Granhaug et al. |
| 8,964,997 B2 | 2/2015 | Gauger, Jr. |
| 8,992,434 B2 | 3/2015 | Halperin et al. |
| 9,072,437 B2 | 7/2015 | Paalasmaa |
| 9,192,326 B2 | 11/2015 | Kahn et al. |
| 2002/0080035 A1 | 6/2002 | Youdenko |
| 2003/0095476 A1 | 5/2003 | Mollicone et al. |
| 2003/0142591 A1 | 7/2003 | Baweja et al. |
| 2006/0017558 A1 | 1/2006 | Albert et al. |
| 2007/0055115 A1* | 3/2007 | Kwok .................. A61B 5/0031 600/300 |
| 2007/0083079 A1 | 4/2007 | Lee et al. |
| 2007/0249952 A1 | 10/2007 | Rubin et al. |
| 2008/0146890 A1* | 6/2008 | LeBoeuf .............. A61B 5/0059 600/300 |
| 2008/0157956 A1 | 7/2008 | Radivojevic et al. |
| 2009/0231964 A1 | 9/2009 | Kraft et al. |
| 2009/0287109 A1* | 11/2009 | Ferren .................. A61B 5/0031 600/549 |
| 2009/0292222 A1* | 11/2009 | Ferren .................. A61B 5/0031 600/549 |
| 2010/0039399 A1 | 2/2010 | Kim |
| 2010/0162169 A1 | 6/2010 | Skarp |
| 2010/0281982 A1 | 11/2010 | Liao |
| 2011/0144455 A1 | 6/2011 | Young et al. |
| 2011/0224510 A1 | 9/2011 | Oakhill |
| 2011/0230790 A1 | 9/2011 | Kozlov |
| 2011/0257772 A1 | 10/2011 | Kerber et al. |
| 2012/0092171 A1 | 4/2012 | Hwang et al. |
| 2012/0327748 A1 | 12/2012 | Lee |
| 2013/0163394 A1 | 6/2013 | Loree, IV |
| 2013/0234823 A1* | 9/2013 | Kahn .................... A61M 21/02 340/3.1 |
| 2013/0289419 A1* | 10/2013 | Berezhnyy ......... A61B 5/02055 600/484 |
| 2013/0289431 A1 | 10/2013 | Gavish et al. |
| 2013/0338446 A1 | 12/2013 | Van Vugt et al. |
| 2014/0088373 A1 | 3/2014 | Phillips et al. |
| 2014/0140567 A1* | 5/2014 | LeBoeuf .............. A61B 5/0408 381/381 |
| 2014/0334645 A1 | 11/2014 | Yun et al. |
| 2014/0371547 A1* | 12/2014 | Gartenberg .......... A61B 5/0048 600/301 |
| 2014/0371635 A1 | 12/2014 | Shinar et al. |
| 2015/0141852 A1 | 5/2015 | Dusanter et al. |
| 2015/0164238 A1 | 6/2015 | Benson et al. |
| 2015/0173671 A1 | 6/2015 | Paalasmaa et al. |
| 2015/0230750 A1 | 8/2015 | McDarby et al. |
| 2015/0258301 A1 | 9/2015 | Trivedi et al. |
| 2015/0263688 A1 | 9/2015 | Nicolino, Jr. et al. |
| 2015/0265212 A1 | 9/2015 | Bruekers et al. |
| 2015/0320354 A1 | 11/2015 | Oakhill |
| 2015/0320588 A1* | 11/2015 | Connor ................ A61F 7/0097 607/107 |
| 2015/0367097 A1 | 12/2015 | Gavish |
| 2016/0015315 A1* | 1/2016 | Auphan ............... A61B 5/4815 600/301 |
| 2016/0035205 A1* | 2/2016 | Messenger ............ A61B 5/746 340/539.15 |
| 2016/0055842 A1 | 2/2016 | DeFranks et al. |
| 2016/0058428 A1* | 3/2016 | Shinar ................ A61B 10/0012 600/301 |
| 2016/0151603 A1* | 6/2016 | Shouldice ................ H04R 3/00 600/28 |
| 2016/0217672 A1* | 7/2016 | Yoon ..................... A61B 5/024 |
| 2017/0061760 A1 | 3/2017 | Lee et al. |
| 2017/0087330 A1* | 3/2017 | Kahn .................... A61M 21/02 |
| 2017/0094385 A1 | 3/2017 | Lee et al. |
| 2017/0149945 A1* | 5/2017 | Lee ..................... H04M 1/6066 |
| 2018/0078197 A1 | 3/2018 | Ware et al. |
| 2018/0078198 A1 | 3/2018 | Reich et al. |

(56) References Cited

U.S. PATENT DOCUMENTS

| | | |
|---|---|---|
| 2018/0078732 A1 | 3/2018 | Keshavan et al. |
| 2018/0081527 A1 | 3/2018 | Dolecki et al. |
| 2018/0082550 A1 | 3/2018 | Read et al. |

FOREIGN PATENT DOCUMENTS

| | | |
|---|---|---|
| EP | 2976993 A2 | 1/2016 |
| JP | 2007244597 A | 9/2007 |
| WO | 2005084538 A1 | 9/2005 |
| WO | 2012051630 A2 | 4/2012 |
| WO | 2013093712 A1 | 6/2013 |
| WO | 2013134160 A2 | 9/2013 |
| WO | 2015006364 A2 | 1/2015 |
| WO | 2015008285 A1 | 1/2015 |
| WO | 2015061579 A1 | 4/2015 |
| WO | 2016035073 A1 | 3/2016 |
| WO | 2016122143 A1 | 8/2016 |
| WO | 2016142793 A1 | 9/2016 |

OTHER PUBLICATIONS

International Search Report and Written Opinion for application No. PCT/US2017/051543 dated Dec. 1, 2017.

\* cited by examiner

FIG. 4

401 — Step 6A

Processor 15 determines biometric parameters for respiration entrainment

402 — Step 6B

Processor 15 determines user preferences for acoustic relaxation by referring to the user profile 30.

403 — Step 6C

Processor 15 select a soundscape that falls within the parameters suggested by the user's profile and/or biometric parameters and arranges the entrainment feature within the soundscape.

404 — Step 6D

Processor 15 reads biometric sensor 19 and adjust the soundscape arrangement or entrainment feature to encourage further relaxation.

SLEEP ASSISTANCE DEVICE FOR MULTIPLE USERS

CLAIM TO PRIORITY AND RELATED APPLICATIONS

This application is a continuation-in-part of U.S. patent application Ser. No. 15/267,567, entitled Sleep Assistance Device, which was filed on Sep. 16, 2016, and is incorporated herein by reference. This application is also related to U.S. patent application Ser. No. 15/267,464, entitled Sleep Quality Scoring and Improvement; U.S. patent application Ser. No. 15/267,552, entitled Intelligent Wake-Up System; U.S. patent application Ser. No. 15/267,848, entitled Sleep System; U.S. patent application Ser. No. 15/267,858, entitled User Interface for a Sleep System; and to U.S. patent application Ser. No. 15/267,886, entitled Sleep Assessment Using a Home Sleep System, all of which were filed on Sep. 16, 2016, and are incorporated herein by reference. This application is also related to U.S. patent application Ser. No. 15/655,845; U.S. patent application Ser. No. 15/655,853; and U.S. patent application Ser. No. 15/655,857 all titled Earphones for Measuring and Entraining Respiration, filed simultaneously with this application, which is incorporated here by reference.

FIELD

This disclosure relates to systems, methods, and apparatuses for aiding multiple users to fall asleep, stay asleep, and achieve a higher quality of sleep throughout the night.

BACKGROUND

Sleeplessness and poor or interrupted sleep may significantly affect a person's health. Poor sleep may be caused by such factors as ambient noise, stress, medical conditions, or discomfort. Thus, there exists a need for a sleep aid that can help address the underlying causes of poor sleep without adversely affecting the user's health in other, unintended ways.

SUMMARY

This disclosure relates to systems, methods, and apparatuses for aiding a user to fall asleep, stay asleep, and achieve a higher quality of sleep throughout the night.

All examples and features mentioned below can be combined in any technically possible way.

In one example, a sleep assistance device is provided for, including a housing; a contactless biometric sensor for determining at least one of a heart rate, a respiratory rate, a presence of a user, or movement of a user; a processor; memory; and a speaker. The processor may be configured to detect a user's sleep state by reading signals from the contactless biometric sensor based on at least one of a detected change in heart rate, body movement, respiration, or a user's presence. The processor may also be configured to initiate a wind-down routine upon detecting a sleep-readiness state, the wind-down routine including at least one of playing relaxing sounds or playing a respiration entrainment sound. The processor may also be configured to play noise-masking sounds upon detecting that a user has fallen asleep and seamlessly transition between the sounds played during the wind-down routine and the noise-masking sounds. In some examples of the sleep assistance device the processor may be configured to detect a sleep-readiness state of a user by reading signals from the contactless biometric sensor and determining that a user is present. In other examples, the sleep assistance device may also include a photodetector and the processor may detect a sleep-readiness state of a user by reading signals from the photodetector and determining that the lights in the vicinity of the sleep assistance device have been turned down.

In some implementations of the sleep assistance device, the relaxing sounds played during a relaxation routine may be a soundscape including at least one sound relating to a scene or place. The respiration entrainment sounds may also be a soundscape including at least one sound relating to a scene or place. In such examples, the processor may be configured to play at least one of the respiration entrainment sounds at a regular interval for respiration entrainment. The processor may be configured to detect a user's initial respiration rate and determine the regular interval for respiration entrainment based on the user's initial respiration rate. The processor may also be configured to periodically detect the user's current respiration rate after determining their initial respiration rate and to adjust the regular interval for respiration entrainment based on the user's current respiration rate. The processor may also be configured to determine an optimal respiration rate for a user and determine the regular interval for respiration entrainment based on the optimal respiration rate.

In other implementations, the sleep assistance device may also include a microphone and the processor may be further configured to detect ambient noise conditions within a sleep space and to select said noise-masking sounds based on the detected ambient noise conditions. The processor may also be configured to seamlessly transition between the sounds played during the wind-down routine and the noise-masking sounds by gradually adjusting the sound properties of the sounds played during said wind-down routine to match the sound properties of the selected noise-masking sounds.

In another example, a sleep assistance device may be provided for, including a housing; a contactless biometric sensor for determining at least one of a heart rate, a respiratory rate, a presence of a user, or movement of a user; a processor; memory; and a speaker. The processor may be configured to detect a user's sleep state by reading signals from the contactless biometric sensor based on at least one of a detected change in heart rate, body movement, respiration, or a user's presence. The processor may also be configured to initiate a wind-down routine automatically upon detecting that a user is ready to sleep. The wind-down routine includes presenting a user with at least one of an end-of-day checklist, home status information, or information regarding the current sleep status of a third party. The wind-down routine may also include playing sounds or music for encouraging relaxation of a user and the processor may be configured to select or arrange the sounds or music based, at least in part, on information received from the contactless biometric sensor or a user profile. In some examples of the sleep assistance device, the processor may be configured to arrange said sounds in the form of a soundscape. The processor may be further configured to arrange said soundscape by selecting, arranging, and mixing the sound elements for the soundscape. The processor may also configured to initiate a sound-masking routine upon detecting that a user has fallen asleep in order to mask ambient noises.

In other examples, the sleep assistance device may also include a microphone for detecting external noises within a room or sleep space. In such examples, the processor may be configured to initiate a sound-masking routine by reading signals from the microphone, analyzing ambient noises detected by the microphone, and selecting, arranging, or mixing a complimentary background sound based, at least in part, on the noises detected by the microphone. The processor may be further configured to arrange the complimentary background sound by selecting, arranging, and mixing the sound elements for a soundscape. The processor may also be configured to gradually transition from the sounds or music for encouraging relaxation to the complimentary background sound A method for helping a user fall asleep may also be provided-for, including the steps of detecting a first biometric indicator of a user including at least one of a heart rate, respiration rate, or presence of a user; based on the first biometric indicator, determining that the user is ready to fall asleep; selecting a first background noise that includes a repeating sound element; arranging the first background noise so that said repeating sound element repeats at a rate that is lower than the detected heart rate or respiration rate of the user in order to reduce the heart rate or respiration rate of a user through entrainment; detecting a second biometric indicator of a user including at least one of a heart rate, respiration rate, or presence of a user; based on the second biometric indicator, determining that the user has fallen asleep; detecting ambient noises; arranging a second background noise for masking the detected ambient noises; and gradually transitioning from the first background noise to the second background noise.

In some examples of the method the first and second background noises include soundscapes associated with naturally-occurring scenes and the at least one repeating sound element is a naturally-occurring sound element within at least one of the scenes. In some examples, the first background noise may be a beach soundscape and the repeating sound element may be the sound of a wave crashing. In other examples, the first background noise may be a forest soundscape and the repeating sound element may be the sound of a frog.

BRIEF DESCRIPTION OF THE DRAWINGS

Various aspects of at least one implementation of a sleep assistance device are discussed below with reference to the accompanying figures. The figures are provided for the purposes of illustration and explanation and are not intended as a definition of the limits of the disclosure.

FIG. 4 is a flowchart showing a potential sequence of steps for a respiration entrainment subroutine in one example of the present disclosure.

DETAILED DESCRIPTION

It should be understood that the following descriptions are not intended to limit the disclosure to an exemplary implementation. To the contrary, it is intended to cover alternatives, modifications, and equivalents as may be included within the spirit and scope of the described subject matter.

Figure 1A:
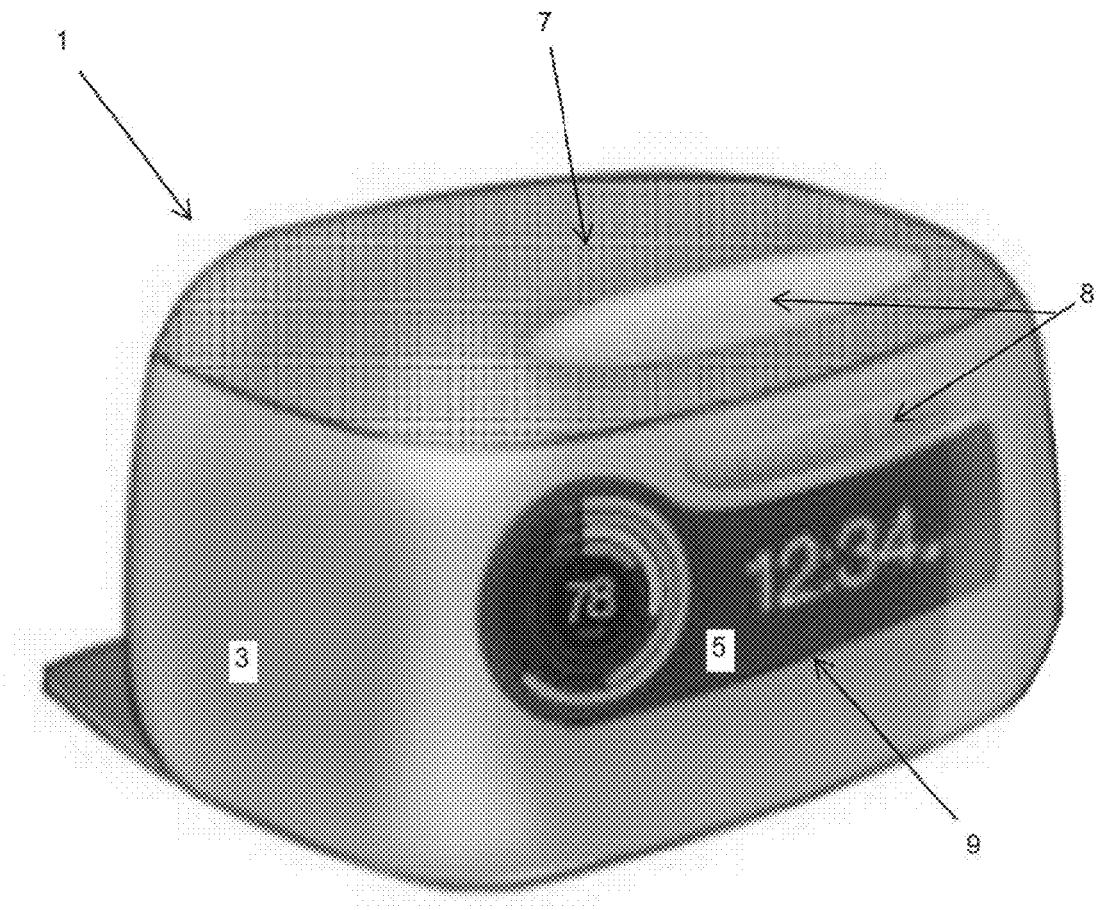
FIG. 1A is a front perspective view of a sleep assistance device with a rectangular housing in one example of the present disclosure.
Figure 1B:
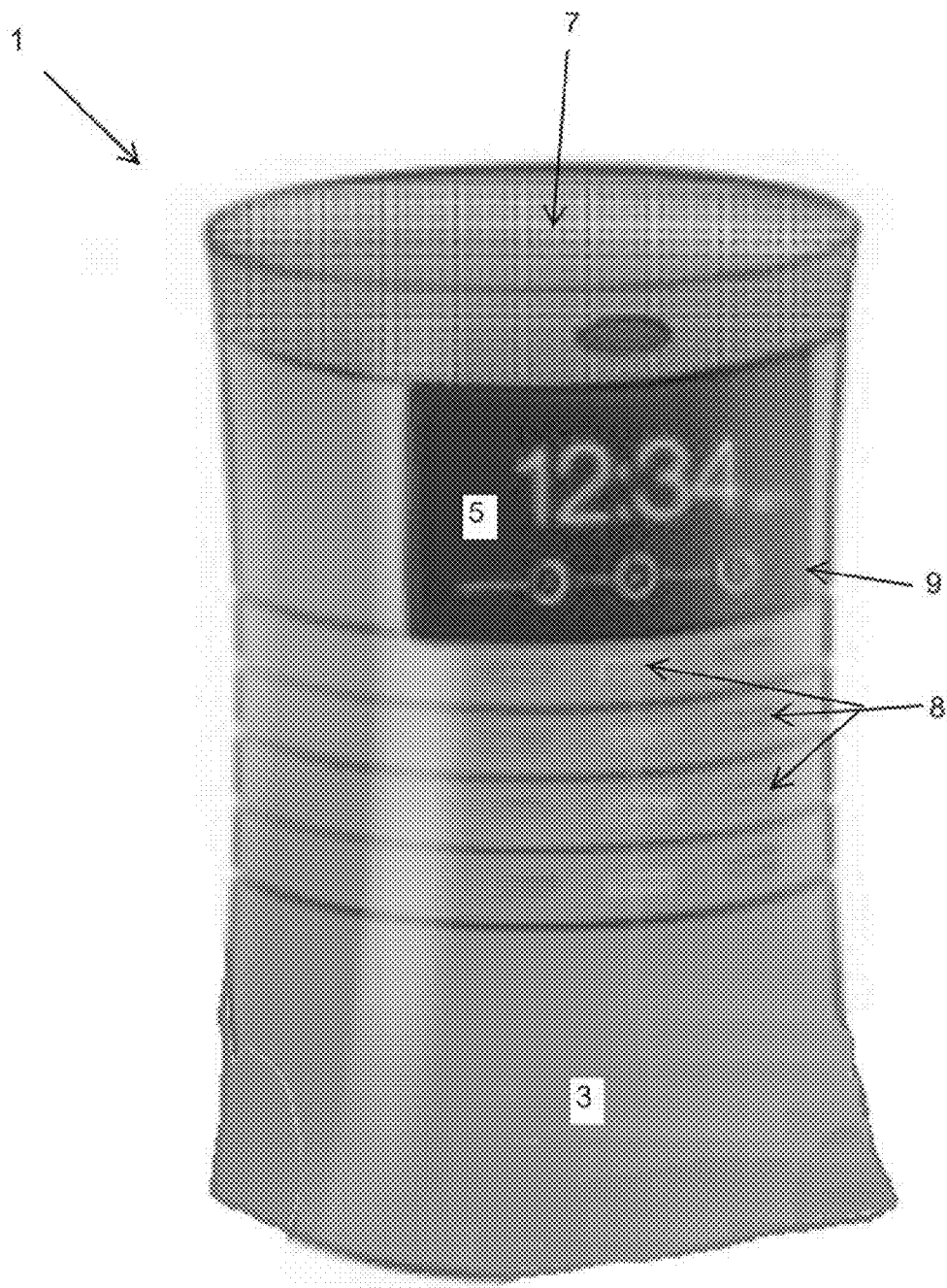
FIG. 1B is a front perspective view of a sleep assistance device with a cylindrical housing in one example of the present disclosure.
Figure 1C:
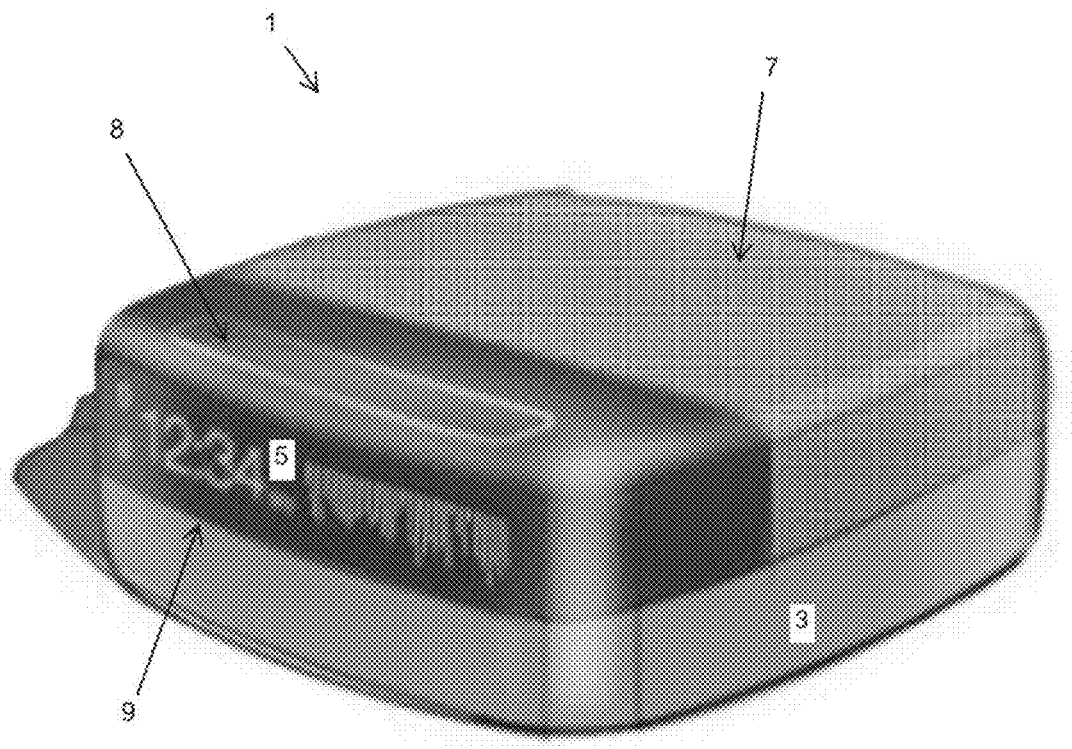
FIG. 1C is a front perspective view of a sleep assistance device with a square housing in one example of the present disclosure.

FIGS. 1A-1C are front perspective views of a sleep assistance device 1 in three examples of the present disclosure. As shown, a sleep assistance device 1 may include a housing 3, a display screen 5, speakers 7, and buttons 8 or a touchscreen 9 for inputting information into the sleep assistance device. A wide variety of forms may be utilized for a sleep assistance device, including a rectangular shape (e.g. FIG. 1A), an elongate cylindrical tower (e.g. FIG. 1B), or a flat square shape (e.g. FIG. 1C). However, as one of ordinary skill in the art will appreciate, any suitable form factor may be utilized that may be suitable for being placed nearby a user while sleeping, such as on a night stand, for example. In such examples, housing 3 may be formed into a suitable shape from any rigid materials, including plastics, metals, wood, or composites.

In some examples, display screen 5 may provide biometric or sleep information gathered by sleep assistance device 1 that may be of interest to a user. Such information may include information regarding the user's biometrics observed during sleep periods, such as information regarding the user's presence, heart rate, heart rate variability, respiratory rate, ambient temperature, movement, snoring, or sleep state over time. This may be direct information or derived information. In some examples, display screen 5 may also include a clock as shown, in FIGS. 1A-1C.

Speakers 7 may comprise any suitable speaker system for generating sounds, as may be familiar to one of ordinary skill in the art. In some examples, speakers 7 may comprise an upwards firing driver along with an acoustic deflector, to provide an omni-directional acoustical experience. Such configurations may be helpful for providing non-directional, room-filling sounds for a soundscape or a white noise while a user is sleeping. Omni-directional sounds systems may be particularly helpful to achieve soothing sounds, a natural wake-up experience, and a consistent listening experience throughout the room. As one of ordinary skill in the art will appreciate, any acceptable sound system for speakers 7 may be employed for producing room-filling sounds, however.

Touchscreen 9 or buttons 8 may comprise any suitable means for delivering inputs to sleep assistance device 1, including a tactile sensor coupled to a surface of housing 3 for detecting the presence of a user's fingers and for detecting pressure, such as when a virtual button on touchscreen 9 is being pressed by a user. Virtual buttons may be displayed on touchpad 9 in a manner familiar to one of ordinary skill in the art in order to allow an operating system to accept input commands from a user. In this manner, sleep assistance device 1 may be configured to accept input commands in a variety of ways and in a variety of contexts, by providing a programmable user interface that may present options and choices to a user via touchpad 9. In other examples, touchscreen 9 may present a permanent display of fixed virtual buttons or include fixed physical buttons 8 for receiving inputs from a user.

In some examples, display screen 5 and a touchscreen 9 may not be necessary or may be reduced in function because a user's smartphone or other external computing device may be used for linking with sleep assistance device 1, displaying information from sleep assistance device 1, accepting inputs, and delivering them to sleep assistance device 1 in order to control its functions. In such a configuration, the display screen 5 and touchscreen 9, if any, may display and control only typical bedside clock-related functions, such as time, alarm, and music selection, or a simplified component of the sleep score, such as just a total score value, may be displayed.

Figure 2:
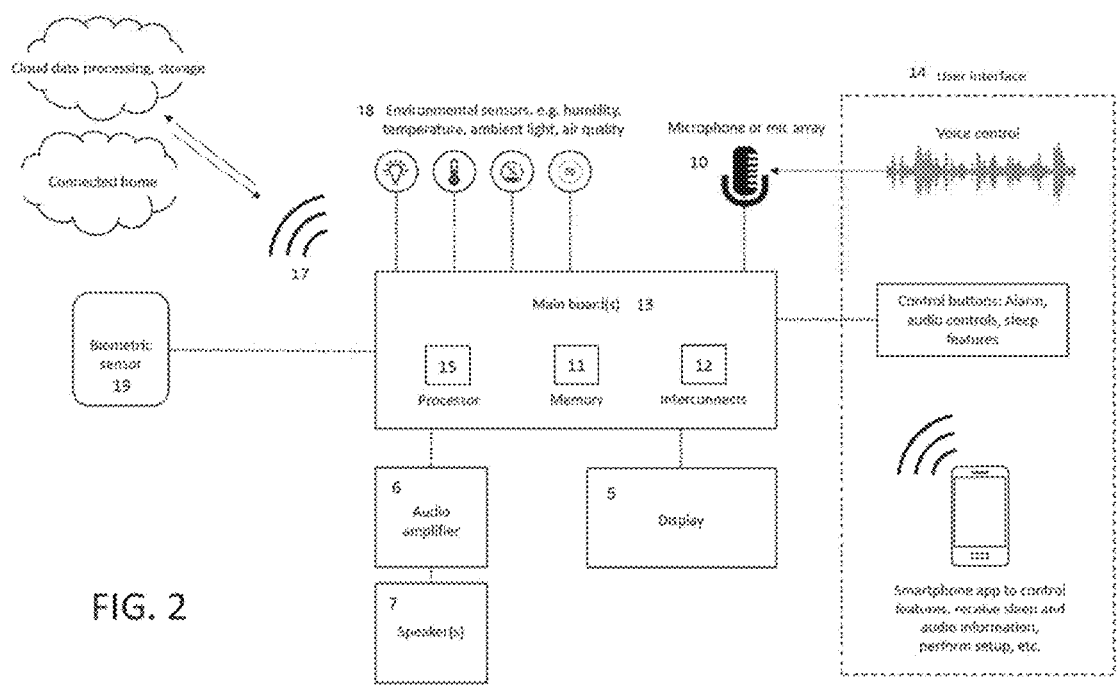
FIG. 2 is a schematic of the components of a sleep assistance device in one example of the present disclosure.

FIG. 2 provides an exemplary schematic of a sleep assistance device, showing its components. As shown, sleep assistance device 1 may include one or more main board(s) 13, including a processor 15, memory 11, and interconnects 12. Main board 13 controls the operation of several other connected components, such as a microphone 10, display screen 5, audio amplifier 6, speakers 7, and buttons 8 or a touchscreen 9 for inputting information into the sleep assistance device. Communications hardware 17 may include any wired or wireless communication means suitable for use with a sleep assistance device, such as WiFi, Bluetooth, USB, micro USB, or any suitable wired or wireless communications technologies known to one of ordinary skill in the art. Main board 13 also receives information from biometric sensor 19 as well any number of environmental sensors 18, for detecting environmental conditions, such as temperature, humidity, ambient light, and air quality. Main board 13 also receives inputs based on a user's interactions with a user interface 14, which may include voice-activated commands detected by microphone 10; various audio, alarm, and sleep control inputs received from buttons 8 or touchscreen 9; or inputs received from a companion application running on a user's smart phone or other external computing device. The communications hardware 17 may also provide communications with external data sources, such as weather reports, and connected home services providing access to such things as lights, thermostat, locks, and any of the sensors 18.

Microphone 10 may be any suitable microphone for detecting and sampling sounds within a user's bedroom or sleep space, as is known to one of ordinary skill in the art. In some examples, microphone 10 may be an arrayed microphone that is suitable for distinguishing between sounds produced by sleep assistance device 1 and sounds produced externally within the user's bedroom or sleep space. In examples where microphone 10 comprises an arrayed microphone, it may comprise a plurality of omni-directional microphones, directional microphones, or any mixture thereof, distributed about sleep assistance device 1. Microphone 10 may be coupled to processor 15 for simultaneous processing of the signals from each individual microphone in a manner familiar to one of ordinary skill in the art in order to distinguish between sounds produced by sleep assistance device 1 and other sounds within the room and to analyze any external noises for use with sound-masking subroutine 27, as discussed below. Microphone 10 may employ beamforming or other techniques to achieve directionality in a particular direction, for example, towards a sound to be analyzed. Microphone 10 may be employed both for monitoring the user's sleep and for receiving spoken user interface commands.

Biometric sensor 19 remotely detects information about a nearby user, including bed presence, respiration rate, heart rate, heart rate variability, or a sleep state among other biometric indicators. In some examples, biometric sensor 19 may be a contactless biometric sensor which may use an RF sensor for directing RF signals towards a user, measuring the strength of the backscattered signal, and analyzing the backscattered signal to determine the state of various vital signs of a user over time. Other contactless biometric techniques may include lasers for measuring minor skin deflections caused by a user's heart rate and blood pressure; or image-based monitoring systems, whereby skin deflections caused by heartbeats and blood pressure may be observed and analyzed over time through a camera. Biometric sensor 19 may be configured to report detected biometric information to processor 15 for storage in memory 11 and to be analyzed for use in the various subroutines described herein.

In other examples, sleep assistance device 1 may also employ a direct biometric sensor as is known to one of ordinary skill in the art. A direct biometric sensor may include probes or contact pads, that may be disposed on or under the user's body or within their mattress or sheets in order to mechanically detect biometric information, such as movement, respiration, heart rate, blood pressure, and temperature, among others. Such sensors may include accelerometers, other motion sensors, or mechanical sensors such as piezoelectric sensors or other vibration sensors. The biometric information detected by the probes may then be communicated to sleep assistance device 1 using a wired or wireless connection in a manner known to one of ordinary skill in the art. In some examples, a biometric sensor may be placed within earbuds worn by a user. Other implementations may combine both contactless and direct biometric sensors. Mechanical sensors that measure the body through an intervening medium, such as bedding, are included in the category of "contactless" biometric sensors.

Figure 3:
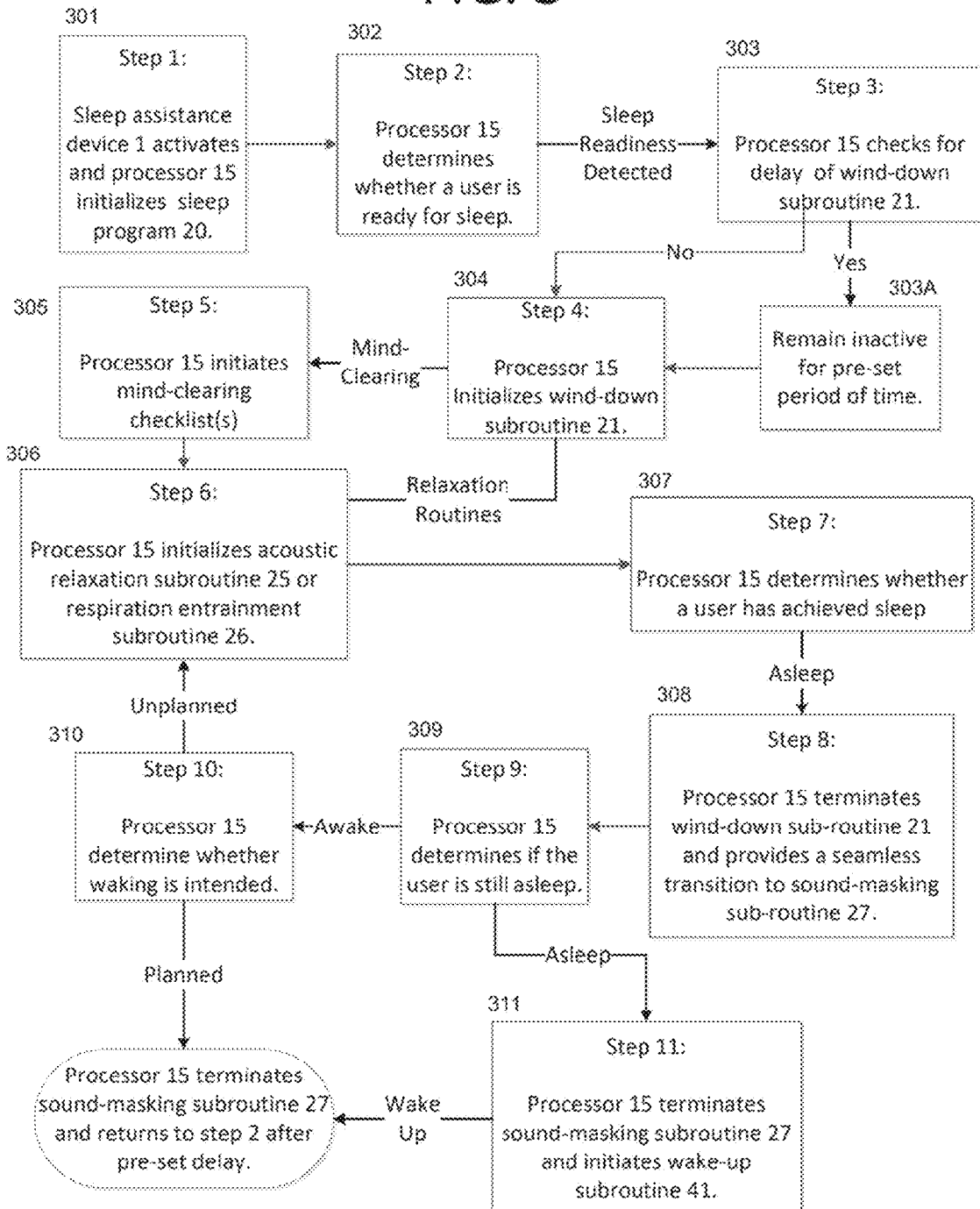
FIG. 3 is a flowchart showing a potential sequence of steps for a sleep assistance program in one example of the present disclosure.

Referring now to FIG. 3, in some examples, processor 15 may initiate a sleep program 20 that may include a series of steps or subroutines to aid a user in achieving longer or higher quality sleep throughout the night, depending on a user's preferences and information supplied by biometric sensor 19. For example, in a first step, sleep assistance device 1 is activated, and processor 15 may initialize a sleep program 20, which may run on a continuous basis or by default (box 301 in FIG. 3). In some examples, a user may be able to selectively deactivate sleep program 20 when it is not necessary. In a second step, processor 15 determines whether a user is ready to sleep, thereby initiating the various subroutines of sleep program 20 (box 302). For example, processor 15 may be configured to read signals from biometric sensor 19 to determine a user's sleep readiness based on a user's presence in bed, room lighting being turned down (based on signals from a photodetector, for example), turning off a TV or radio, or based on a pre-set bed time defined by a user. Additional sleep readiness indicators may be observed by sleep assistance device 1. Preferably, such indicators may be passively observed without the need for a user to manually indicate that they are preparing for sleep (e.g. by pressing a button). Information about the state of external devices may be observed by sensors in the sleep assistance device 1, or through integration with a home-automation system.

In some examples, processor 15 may initiate a wind-down routine immediately upon detection of a sleep readiness indicator by the sleep assistance device. In other examples, however, processor 15 may initiate wind-down routine 21 at an established interval after detecting a sleep readiness indicator. For example, a user may wish to begin the wind-down routine after first having an opportunity to read in bed or engaging in any other desired activity. Thus, in a third step, processor 15 may delay initiating wind-down subroutine 21 based on a user's preference that may be input by a user (box 303 and 303A). Such delays may be pre-programmed or configurable by a user. If no sleep readiness indicator is detected, processor 15 may be configured to re-check for sleep readiness either periodically or continually.

Once biometric sensor 19 detects a sleep readiness indicator and any pre-set delay time has lapsed, processor 15 may initiate a wind-down subroutine 21 in a fourth step (box 304). Once wind-down routine 21 has been activated, processor 15 may initiate a series of steps to condition the user for higher quality rest, including initiating a mind-clearing subroutine 23, an acoustic relaxation subroutine 25, or a respiration entrainment subroutine 26.

In a fifth step, wind-down subroutine 21 may begin, in some examples, with a mind-clearing subroutine 23 (box 305). Mind-clearing subroutine 23 is designed to help a user clear their mind of thoughts and concerns that may remain with the user at the end of the day, thereby adversely affecting sleep. During mind-clearing subroutine 23, processor 15 may present the user, via user interface screen 5, verbal commands, or an external computing device, with a checklist of information relevant to the user's day. For example, a user may be prompted with the events scheduled in the user's calendar for that day, which may be checked-off as completed or otherwise addressed. Processor 15 may also present information regarding the status of various in-home systems by accessing information provided by a home automation system, if present, such as the thermostat settings, door lock status, or garage door status. In other examples, processor 15 may receive information from other devices to check on the sleep state of a user's child or other family members in the house, in order to confirm that other people are already asleep. In a similar manner, processor 15 may add any user-defined end-of-day items to a checklist so as to help clear the user's mind before sleeping. Furthermore, during mind-clearing subroutine 23, processor 15 may communicate with any available external systems, such as a user's calendar or home automation system, in order to put a user's mind at ease before sleeping.

At step six, wind-down routine 21 may also include an acoustic relaxation subroutine 25 (box 306). Once acoustic relaxation subroutine 25 has been activated, processor 15 begins playing a series of recordings or sounds designed to relax a user, which may lower the user's respiration rate, heart rate, blood pressure or overall stress levels prior to sleeping. For example, processor 15 may select songs with a relaxing tempo, in a manner known to one of ordinary skill in the art. In other examples, sleep assistance device 1 may select songs that have been observed in the past to relax the current user or a population or users. In such examples, a local or online database of songs may be searched to identify a song file having acoustic properties matching a user's preferences. Processor 15 may further be configured to manage attributes of the music such as the volume level, tempo, or dynamic range in order to achieve optimal relaxation. The acoustic relaxation subroutine 25 may be performed at the same time as the mind-clearing subroutine 23, or they may be performed sequentially, depending on the user's preferences or other configuration parameters.

Other relaxations subroutines may be executed at step 6 of wind-down routine 21, such as a respiration entrainment subroutine 26. This may be used after the relaxation subroutine 25 or in place of it. To help the user fall asleep, one prominent sound element within a soundscape, such as a frog in a forest scene, or a wave in a beach scene, is used as an entrainment feature. The selected sound element is played at intervals that are slightly slower than the respiratory rate of the user, based on signals received from biometric sensor 19. As the user's respiratory rate slows to match the intervals of the entrainment feature, processor 15 detects the reduction through biometric sensor 19. Processor 15 then makes a corresponding adjustment in the intervals at which the entrainment feature is played, thereby encouraging yet further reduction in respiratory rate until optimal vital signs for sleep are achieved. Once biometric sensor 19 detects that a user has fallen asleep (box 307 and 308) the entrainment subroutine stops, and the system moves on to the next subroutine. In some examples, the selected sound element and entrainment feature may remain an inconspicuous feature within the overall soundscape and may only impact the user's respiration rate in a subliminal manner. In other examples, the entrainment sound is more prominent, and the user is encouraged to consciously attempt to synchronize their breathing with it.

FIG. 4 is a flowchart showing a potential sequence of steps for performing respiration entrainment subroutine 26. To begin, in step 6A, processor 15 determines a user's biometric parameters for respiration entrainment (box 401 in FIG. 4). Processor 15 reads signals from biometric sensor 19 to determine a user's current biometrics, such as heart rate and respiration rate. At step 6B, processor 15 may assesses the user's preferences and history by referring to a user's relaxation profile 30, which may be data stored in memory 11 and containing information regarding what acoustic conditions have or have not helped to achieve a relaxed state for the user in the past (box 402).

User profile 30 may be created for a user or for multiple users during an initial setup process, and may be re-configured over time. In some examples, user profile 30 includes a user's preferences for the types of sounds to be used. In other examples, processor 15 automatically populates the user profile continuously by observing a user's response to certain relaxation techniques, as observed through biometric sensor 19. In some implementations, the relaxation profile correlates a user's acoustic preferences to the user's current biometric readings, as determined at step 6A. In referring to user profile 30, processor 15 assess a user's acoustic preferences regarding such factors as: 1) which soundscapes a user prefers, 2) the user's volume preferences, or 3) the user's pitch and tempo preferences, among other things, based on similar observed biometric conditions in the past.

At step 6C, entrainment subroutine 26 selects a soundscape that falls within the parameters suggested by the user's profile 30 (box 403). The soundscape may be selected by processor 15 based on the user's history within the user profile or may be manually selected by a user in some examples. Once a suitable soundscape has been selected, processor 15 plays sounds associated with a relaxing scene or environment, such as a beach, a forest, a brook, traffic, city sounds, or a light rain. In some examples, processor 15 may play pre-recorded examples of such sounds on a repeating basis. However, this approach may result in periods of repetition as the recorded sounds necessarily repeat in order to provide a continuous soundscape. These instances of repetition may actually deter relaxation or sleep when a user becomes aware of them and begins focusing on them. In preferred implementations, the individual sound elements of such relaxing scenes and environments (e.g., a cricket or frog in a forest scene or a seagull sound in a beach scene) are provided as independent sound records in memory 11, which are mixed and played at random or semi-random intervals by processor 15 in order to provide a continuous and more-natural soundscape, which minimizes the noticeability of any looping.

Each available soundscape is produced when processor 15 executes a soundscape program stored in memory 11, which provides or identifies a collection of sound records associated with the selected soundscape (e.g. a forest or seaside, or fireplace soundscape program). The soundscape program may include instructions for mixing the various sound records representing the individual sounds comprising the soundscape. These may include instructions regarding repetition, pitch, or volume of each individual sound record, among any other acoustic factors known to one of ordinary skill in the art. In some examples, the soundscape programs include default settings for mixing the relevant sound records. In other examples, the settings may be adjusted by processor 15 based on a user's profile or by user input. When a respiration entrainment feature has been selected, processor 15 will arrange one sound record among the set of sounds records included within the soundscape program as an entrainment feature. To do so, processor 15 arranges the sound to be played at an interval that will encourage a user to reduce their respiration rate so as to achieve an optimal respiration rate.

At step 6D, processor 15 may adjust the period of repetition, volume, tempo, or pitch settings of individual sound elements while observing any changes in biometric indicators, such as heart rate, respiration, or movement, in order to determine an optimal setting for each individual sound element (box 404). For example, processor 15 may take additional readings from biometric sensor 19 in order to determine whether a user has matched their respiration rate to the same intervals as the entrainment feature within the soundscape. Where additional reductions in respiration rate are desired, processor 15 may further reduce the period of repetition for the entrainment feature, until optimal respiration is achieved. In other examples, a user may be able to adjust the relative settings of individual sound elements manually, so as to override the settings automatically determined by entrainment subroutine 26. Any biometric feedback or manual changes observed by sleep assistance device 1 may be recorded in a user's profile 29 in order to provide a more customized entrainment feature or relaxation experience in the future.

Returning again to FIG. 3, at step 7, processor 15 determines, on a periodic or continual basis, whether a user has begun actively sleeping (box 307). To do so, processor 15 reads signals from biometric sensor 19 to determine whether there has been a measurable change in heart rate, respiration, body movements, or any other biometric indicator of sleep known to one of ordinary skill in the art. Processor 15 then activates a sound-masking subroutine 27, which is intended to aid in keeping a user asleep and helping them achieve better quality sleep by producing a white noise or soundscape that is selected or modified to optimally mask the ambient noises within the room (box 308). To avoid disturbing the user during the transition from the relaxation or entrainment subroutines to the masking subroutine, the same sounds are used, at least initially, with their properties modified gradually to make the transition from one mode to the next less disruptive. For example, if a wave crashing was used as the entrainment feature, the last wave sound of the entrainment mode is allowed to finish before the switch takes place, and wave crashes continue to feature in the masking mode, but now at a random interval and at a volume determined by the masking subroutine 27. In this way, the user is not disturbed from sleep by the sudden change in soundscape.

Figure 5:
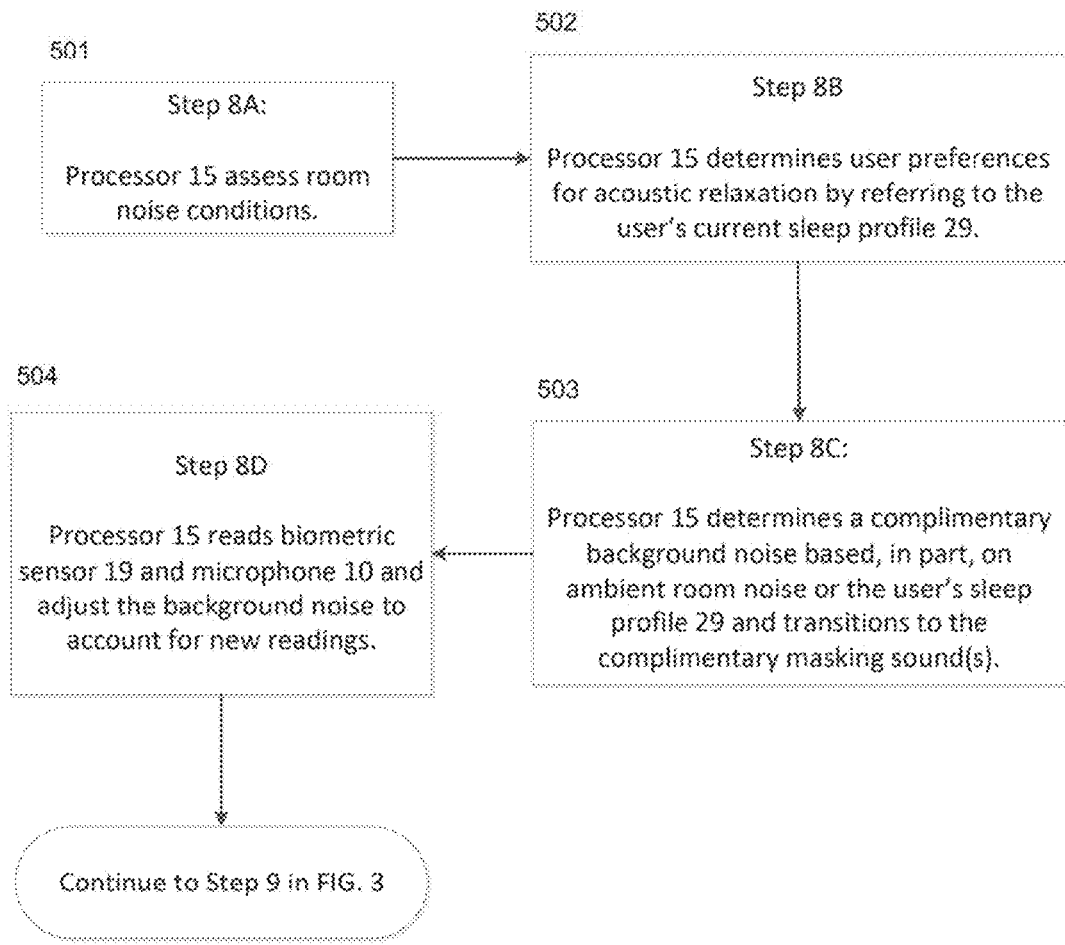
FIG. 5 is a flowchart showing a potential sequence of steps for a sound-masking subroutine in one example of the present disclosure.

FIG. 5 is a flowchart showing an example sequence of steps for sound-masking subroutine 27. At step 8A, processor 15 receives information regarding ambient noises detected within the room from microphone 10 which, as discussed above, may be a microphone array in order to distinguish between sounds produced by sleep assistance device 1 and external noises occurring within a user's bedroom or sleep space (box 501 in FIG. 5). Echo-cancellation may also be used to remove the sounds produced by the sleep assistance device from the microphone signal. As processor 15 receives information regarding the noise properties of a user's room via microphone 10, it analyzes information regarding room noise, including identifying particular sounds, along with its volume, pitch, tempo, or other acoustic properties of interest on a continual basis.

At step 8B, processor 15 determines user preferences for noise masking by referring to the user's current sleep profile 29, which may be a database stored in memory 11 (box 502). Sleep profile 29 may correlate user preferences with a user's biometric readings and room noise conditions determined at step 8A. To determine a user's noise masking preferences, processor 15 references a user's preferences regarding various factors, including whether the user prefers music, soundscapes, or white noise; the user's volume preferences, and the user's pitch and tempo preferences. These preferences may be based on past biometric readings, room noise conditions, or past user inputs. In some examples, sleep profile 29 is not used, and processor 15 selects noise-masking sounds based on the observed room noises, alone.

In step 8C, as processor 15 continues to analyze the noise properties of the sleep space, it simultaneously selects complimentary background noise (box 503). The noise may be loaded from memory 11 or from a network library of sounds including songs, white noise, and soundscapes, which may have similar acoustic properties to the noise, making it well-suited for masking observed external noises. In some examples, processor 15 generates the background noise from complimentary sounds associated with a relaxing scene or environment, such as those employed through acoustic relaxation subroutine 25 and entrainment routine 26 (as discussed above). In such examples, the individual sound elements of a relaxing scene or environment may compliment the acoustic properties of the ambient noises detected within the sleep space. For example, sound elements employed as part of a soundscape having similar properties to a detected sound (e.g. waves on a beach may be determined to be complimentary to the sound of cars travelling on a nearby road) may be configured to match the analogous, external noises as closely as possible, for example, by matching the pitch, volume, or the tempo of such detected noises.

Also at step 8C, once processor 15 selects and arranges a complimentary background noise it transitions the sounds being played during the prior entrainment or relaxation subroutines into the sounds played during sound-masking subroutine 27. To do so, processor 15 uses the same sounds, at least initially, with their properties modified gradually to make the transition from one mode to the next less disruptive. For example, if a wave crashing was used as the entrainment feature during a prior respiration entrainment subroutine, the last wave sound is allowed to finish before beginning to transition to the complimentary sounds selected for the sound-masking subroutine. The wave crashes may also continue to feature in the sound-masking mode, but now at a random interval and at a volume determined by the masking subroutine 27. In this way, the user is not disturbed from sleep by the sudden change in soundscape.

As with entrainment subroutine 26, processor 15 may periodically adjust the acoustic properties of individual sound elements within a soundscape during sound-masking subroutine 27, in response to changes in a user's sleep state. In step 8D, for example, based on the data received from biometric sensor 19, the processor 15 adjusts the soundscape to increase the masking level when it appears that the user was disturbed by a sound in the environment (box 504). The system may also monitor the user's sleep state to determine whether such periodic adjustments are preferable or detrimental to user's sleep patterns, and update a user sleep profile 29 in memory 11, if appropriate. In this way, sleep assistance device 1 may become better-adapted to a particular user's sleep patterns and preferences over time, thereby providing healthier, deeper, and less interrupted sleep.

Referring again to FIG. 3, processor 15 also determines whether a user remains asleep. At step 9, processor 15 receives signals from biometric sensor 19 and determines whether a user has awoken based, for example, on a detected change in heart rate, respiration, or movement (box 309). At step 10, processor 15 determines whether the incidence of waking was planned or unplanned, indicating interrupted sleep (box 310). In some examples, processor 15 makes this determination by comparing the current time to a user's pre-defined waking timeframe, alarm settings, or the user's historic waking timeframe for that day of the week. If the present time falls prior to an appropriate waking time, processor 15 determines that the user has awoken prematurely and sleep program 20 may return to step 6 and re-initiate the acoustic relaxation subroutine or entrainment subroutine in order to re-establish normal sleep. On the other hand, if processor 15 determines that the instance of waking was planned, processor 15 terminates noise-masking subroutine 27 and restarts sleep program 20 after a pre-set delay time, in order to allow the user time to vacate the sleep space.

In some examples, sleep assistance device 1 also provides a wake up alarm or signal based on information received from other sleep assistance devices within the home or other external systems linked with sleep assistance device 1. For example, processor 15 may trigger a wake up alarm based on a significant disruption in a child's sleep pattern detected by another device within the home. In other examples, processor 15 may wake a user if material changes in the home's operation are detected by a home automation system, such as a significant, unplanned temperature drop within the home or the activation of a smoke alarm or motion sensor.

In some examples, processor 15 logs the signals received by biometric sensor 19 throughout the night. Details logged may include recorded wake-up events, frequency of movement, heart rate, respiration, or any other information regarding a user that is observed by biometric sensor 19. Information detected by microphone 10 may also be logged, such as instances of snoring, sleep apneas, or sleep-talking, among others. Any information relevant to the quality or duration of a user's sleep may be received by processor 15, logged in memory 11, and displayed on user interface screen 5 or an external computing device, where the information may be displayed along with a report regarding the relative quality and duration of the user's sleep.

Figure 6:
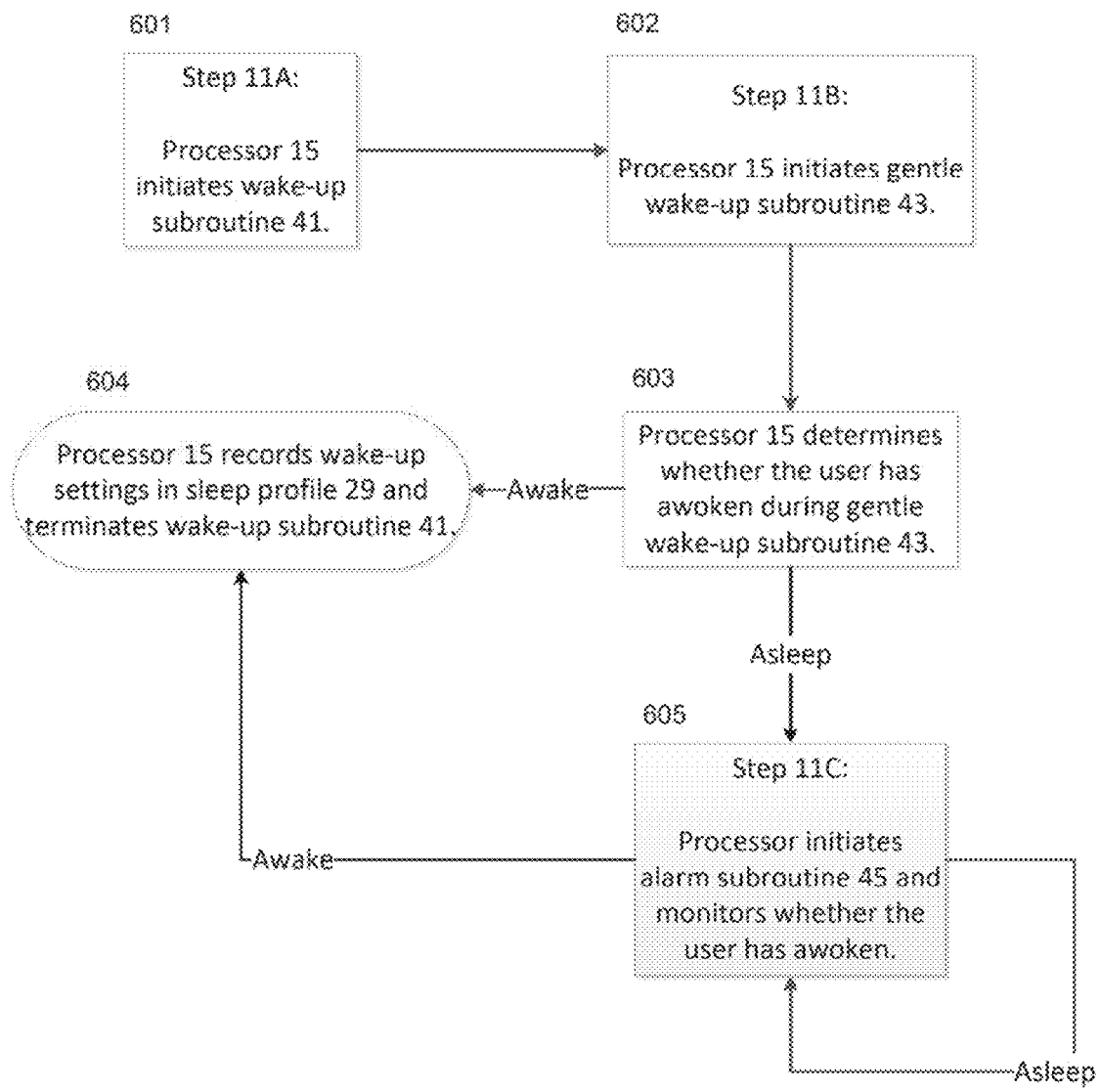
FIG. 6 is a flowchart showing a potential sequence of steps for a wake-up subroutine in one example of the present disclosure.

As shown in FIG. 3, where a user continues to sleep through the night, processor 15 may eventually terminate sound-masking subroutine 27 and initiate a wake-up subroutine 41 in order to awaken a user deliberately at step 11 (box 311). FIG. 6 is a flowchart showing an example sequence of steps for a wake-up subroutine 41. In instances where a user does not wake prematurely or on their own, sleep assistance device 1 enters a wake-up subroutine 41 to help users wake up in a comfortable and healthier manner. At step 11A, processor 15 may initiate wake-up subroutine 41 based on a pre-defined wake-up time or based on the observed biometrics of a user or a combination thereof (box 601 in FIG. 6). For example, processor 15 may initiate wake-up subroutine 41 only after a user has been observed by biometric sensor 19 to have slept for a desired amount of time or has achieved a predetermined level of sleep quality (such as REM sleep or NREM sleep) for a desired period of time. In other examples, a user may define a desired wake-up window, which indicates the earliest time at which a user may be awoken, provided that sleep assistance device 1 has determined that sufficient sleep has taken place, or a latest time, by which the user must be awoken, regardless of the amount of sleep they have had. In instances where a user is approaching a pre-defined final wake-up time, wake-up subroutine 41 may initialize in advance of the final wake-up time in order to provide for sufficient time to enter into a gentle wake-up subroutine.

At step 11B, processor 15 enters a gentle wake-up subroutine 43 (box 602). During gentle wake-up subroutine 43, processor 15 continues playing the music, soundscape, or white noise or other sounds that had been playing during the prior operation of sound-masking subroutine 27. However, in gentle wake-up subroutine 43, processor 15 gradually alters the acoustic properties of the sounds so as to gradually raise the consciousness of a user from sleep without alarming the user's nerves or "shocking" them out of sleep as a with a traditional alarm clock. For example, processor 15 may gradually alter the volume or pitch of any currently-playing white noise or soundscape. Processor 15 may also alter the operation of any currently running soundscape program by introducing new sound records into the soundscape program, such as sound records associated with a morning timeframe for the given soundscape. For example, where owl or cricket sound records were mixed into a soundscape during sound-masking subroutine 27, sound records associated with morning songbirds are introduced into the soundscape program during the gentle wake-up subroutine. Where an urban soundscape is used, for example, sound records such as delivery trucks or the sound of shops opening for business may be used. Thus, the soundscapes generated by sleep assistance device 1 change in gentle-wake up subroutine to reflect a morning setting for the selected soundscape. Such natural morning transitions within a consistent soundscape setting may further aid a user in waking naturally and gradually from sleep. Where music is being utilized by sound-masking subroutine 27, processor 15 may also begin selecting songs with acoustic properties that are somewhat less conducive to continual sleep, while also adjusting the volume, in order to begin encouraging a user to wake up.

Processor 15 may also adjust the acoustic properties of the sounds being played by sleep assistance device 1 during the gentle wake-up subroutine with reference to the information contained in sleep profile 29. For example, sleep profile 29 may include data regarding acoustic properties (such as the volume, pitch, or other acoustic properties) that are likely to wake a given user from sleep (e.g., an alarm sound), based on past observations from biometric sensor 19. In this case, processor 15 may gradually transition the acoustic properties of the sounds being played by sleep assistance device 1 towards an alarm sound while avoiding acoustic properties that are likely to completely wake the user. In some implementations, gentle wake-up subroutine 41 is configured to gradually transition sleep assistance device 1 from the sound settings employed during sound-masking subroutine 27 to the sound settings employed during an alarm subroutine 45 (described below). If a user does awaken during gentle wake-up subroutine, biometric sensor 19 indicates that the user has awoken and processor 15 may record the wake-up event and current acoustic settings in sleep profile 29 to further refine the acoustic settings that are employed in the future during gentle wake-up subroutine 43. Once the gentle wake-up subroutine 43 has been initiated, processor 15 also begins checking to determine wither the user has awoken, based on signals received from biometric sensor 19 (box 603). If so, processor 15 records the wake-up settings in sleep profile 29 and terminates wake-up subroutine 41 (box 604). If the user has not awoken during gentle wake-up subroutine 43, wake-up subroutine 41 proceeds to step 11C.

At step 11C, processor 15 initializes alarm subroutine 45 when it determines that the user's final wakeup time has been reached without the user awakening (box 605). When alarm subroutine 45 is activated, processor 15 continues playing the music, soundscape, white noise or other sounds that had been playing during the prior operation of gentle wake-up routine 43. However, in alarm subroutine 45, processor 15 alters the acoustic properties of the sounds so as to fully awaken the user. For example, processor 15 may further alter the volume or pitch of any currently-playing white noise or soundscape beyond a level that is likely to wake the user, based on the information stored in sleep profile 29. Processor 15 may also alter the operation of any currently running soundscape program by introducing more disruptive sound records associated with a morning timeframe for the given soundscape. For example, where a forest soundscape is utilized, alarm subroutine 45 may select additional, more disruptive bird calls or animal sounds or increase the regularity of such sound records within the soundscape mix. Where an urban soundscape is used, sounds such as honking horns or jack-hammers may be added. Thus, the soundscapes generated by sleep assistance device 1 change in alarm subroutine 45 to continue reflecting the sounds associated the selected soundscape, while ensuring that a user will awaken based on the sounds presented. Again, a consistent soundscape setting further aids a user in waking naturally from sleep in a less shocking manner. Where music is being used by sound-masking subroutine 27, processor 15 may, during alarm subroutine 45, begin selecting songs with acoustic properties that are highly likely to wake a user from sleep, while also adjusting the volume, in order to begin encourage a user to wake up.

As with the gentle wake-up phase, processor 15 may refer to sleep profile 29 to determine the appropriate sound records, acoustic properties, or songs for waking a user during alarm subroutine 45, based on past observations from biometric sensor 19. Where a user has not awoken despite the initiation of alarm subroutine 45, processor 15 may continue to alter the acoustic properties of the sound played by sleep assistance device 1 in a manner more disruptive to sleep until the user has awoken. In such instances, biometric sensor 19 indicates when the user has eventually awakened and processor 15 may record the wake-up event along with the current acoustic settings in sleep profile 29 to further refine the acoustic settings that are employed in the future during alarm subroutine 45 (box 604).

Thus, in some implementations, a continual soundscape is maintained throughout a user's sleep progression. For example, a consistent soundscape can be employed during relaxation subroutine 25 or respiration entrainment subroutine 26, sound-masking subroutine 27, gentle wake-up subroutine 43, and alarm subroutine 45. By employing a consistent soundscape scene, such as a beach, a forest, a city, or a brook, throughout the user's sleep progression, users are likely to enjoy longer or higher quality, uninterrupted sleep without the disruption caused by abrupt or unexpected changes to the acoustic properties of their bedroom or sleep space. By providing for a consistent acoustic framework, the properties of which change gradually throughout the user's sleep cycle in order to adapt to the user's needs, the present disclosure provides a helpful sleep system for a user.

Adding a Second Sleeper

In many cases, two people share a single bed. This presents at least two complications for the system described above. First, the additional person's respiration, heart beat, and movement may cause inaccurate readings in the biometric sensors focused on the first person. Second, sounds used to entrain the breathing of the first person may not be properly timed to also entrain the second person, and even if they are, the system may detect that one person is asleep and switch to masking sounds before the other person is also asleep. Conversely, continued entrainment sounds may reawaken the first person to fall asleep or cause that person's sleep to be less restful.

Figure 7:
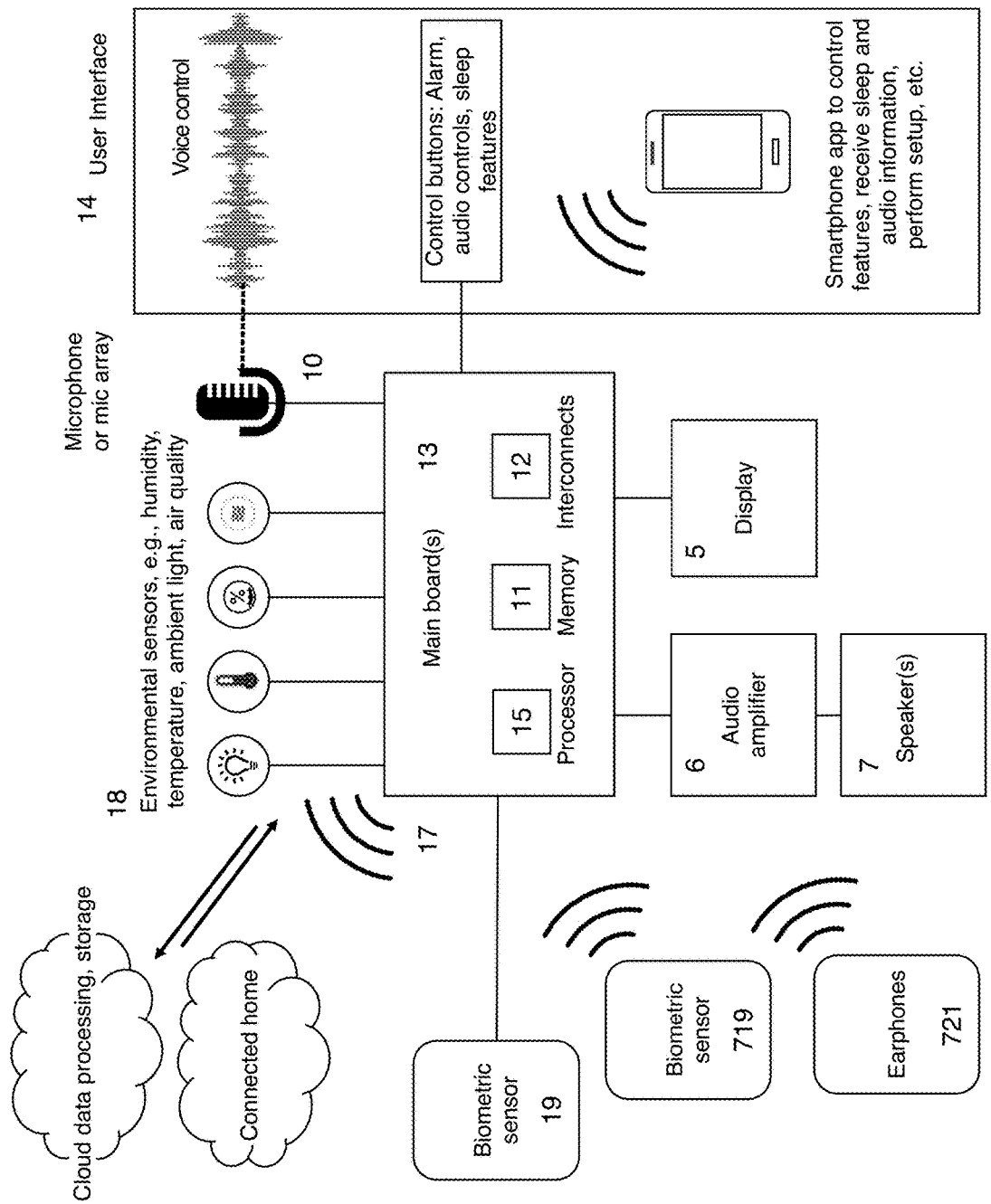
FIG. 7 is a schematic of the components of a sleep assistance device in another example of the present disclosure.

This situation can be addressed through the addition of two separate items to the system, as shown in FIG. 7. To address the problem of the second user's presence confusing the first biometric sensor 19, a second biometric sensor 719 is added. In some examples, the first biometric sensor 19 is integrated into the sleep system 1 and positioned on one side of the bed. The second biometric sensor is located on the other side of the bed so that it detects the respiration or other biometric readings of the second user. The two biometric sensors do not have to be of the same type. For example, the integrated sensor 19 may be a radar-type sensor, while the second sensor is a mechanical sensor. In other examples, the two sensors are both radar-based, and various methods are available for preventing the signals of the two radar emitters from interfering with each other. See, for example, U.S. Pat. No. 8,941,431. A method of distinguishing the signals of two users, detected through two sensors, is described in U.S. Patent Publication 2015/0173671. FIG. 7 shows that the second sensor 719 is connected to the system wirelessly. Example connection technologies include Bluetooth or WiFi, as well as other standard or proprietary connections. In other examples, the second sensor may be wired.

In other examples, two entire sleep systems are used, one for each user, and located on either side of the bed. In this case, each system uses its own integrated sensor 19, and produces sounds based on its own user's respiration and sleep state. Depending on the range of the sensors and the audibility of the output audio, the two systems may need to coordinate with each other. Such coordination may include sharing data from the sensors to help each system exclude the other system's user's data from its own, and coordinating their audio output so that they do not interfere with each other. In some examples, where the first user falls asleep before the second, the first user's system may change the level or character of the masking sounds it produces to particularly mask out the wind-down sounds still being provided by the second user's system.

To address the problem of the entrainment or masking sounds for the two users interfering, when only one sleep system is used (and therefore only one speaker on one side of the bed), the second user may use earphones 721. In particular, earphones specifically designed for being worn while sleeping are described in U.S. patent application Ser. No. 15/106,989, filed Jun. 21, 2016, published as U.S. Publication No. 2017/0094385; Application Ser. No. 15/348,400, filed Nov. 10, 2016, published as U.S. Publication No. 2017/0149945; and application Ser. No. 15/352,034, filed Nov. 17, 2016, published as U.S. Publication No. 2017/0061760 all titled Intelligent Earplug System and incorporated here by reference. Depending on the user's comfort levels, conventional headphones or earphones of any type could also be used. Such earphones can be used to provide the respiration-entraining and, later, masking sounds and wake-up sounds for the second user without disturbing the first user. The earphones can also block the second user from being disturbed by the sounds from the sleep system, both by passively (or actively) blocking ambient sound, and through the masking effects of the sounds the earphones produce. The sleep system 1 can be substituted for the smartphone used to control the intelligent earplugs in the above-mentioned applications, providing the entrainment sounds or timing information to the earphones wirelessly. One particular feature of the intelligent earplugs is that the smartphone controlling them only periodically communicates with them, rather than continuously streaming audio, to preserve battery life and minimize RF emissions. When the sleep system 1 is used to control the intelligent earplugs, it can similarly minimize communications by only sending changes to respiration rate and sleep state, and allowing the intelligent earplugs themselves to adjust the timing of their playback of stored respiration entraining sounds and then switch to stored masking sounds. At the end of the night, earphones controlled by the sleep system 1 can also be used to wake the second user without disturbing the first user, or to mask the sounds used to wake the first user so that the second user is not awoken.

In a situation where more than two people share a sleeping space, such as military barracks, additional sensors may be used, though separating their respective biometric data may become increasingly difficult. One solution to this problem, which also simplifies the two-user problem, is to embed the additional sensors in the earphones described above, which is further described in related U.S. Patent Applications: Ser. No. 15/655,845, filed Jul. 20, 2017, published as U.S. Publication No. 2019/0022348; 15/655,853, filed Jul. 20, 2017, published as U.S. Publication No. 20190022349A1; and Ser. No. 15/655,857, filed Jul. 20, 2017, published as U.S. Publication No. 2019/0028789, mentioned above. In this way, the data from each of the additional sensors is reliably associated with the correct user or users.

In other examples, it may be desirable for each user's sensing- and entraining-earphones to be managed by that user's smart phone, rather than by the central system, with the smart phone(s) reporting their user's status back to the central system to help screen out the additional user's respiration from that of the first user as detected by the first sensor 19. Reporting other user's sleep state back to the central system, even if the additional users are not sharing a bed with the first user, may provide other benefits, such as coordinating wake-up alarms and home-automation system events related to the various user's sleep states. The same goes for use of multiple sleep systems at one or multiple beds. In the case that every user has smart earphones and an associated smart phone, the central system that coordinates them may be off-site, i.e., cloud-based, and implement only some of the features of the system 1 related to coordinating the sleep state of the various users.

One of skill in the art will appreciate that the systems, methods and apparatuses outlined above may include various hardware and operating software, familiar to those of skill in the art, for running software programs as well as communicating with and operating any devices, including, for example, a biometric sensor, environmental sensors, a user interface, a computer network, a sound system, and any other internal or external devices. Such computerized systems may also include memory and storage media, and other internal and external components which may be used for carrying out the operations of this disclosure. Moreover, such computer systems may include one or more processors for processing and controlling the operation of the computer system, thus, embodying the processes of this disclosure. To that end, the processor, associated hardware and communications systems may carry out the various examples presented herein.

While the disclosed subject matter is described herein in terms of certain exemplary implementations, those skilled in the art will recognize that various modifications and improvements can be made to the disclosed subject matter without departing from the scope thereof. As such, the particular features claimed below and disclosed above can be combined with each other in other manners within the scope of the disclosed subject matter such that the disclosed subject matter should be recognized as also specifically directed to other implementations having any other possible permutations and combinations. It will be apparent to those skilled in the art that various modifications and variations can be made in the systems and methods of the disclosed subject matter without departing from the spirit or scope of the disclosed subject matter. Thus, it is intended that the disclosed subject matter include modifications and variations that are within the scope of the appended claims and their equivalents.

What is claimed is:

1. A sleep assistance device comprising:
a housing;
a first contactless biometric sensor, integrated into the housing, for determining at least one of a heart rate, a respiratory rate, a presence, or movement of a first user;
a processor;
memory; and
a speaker;
wherein said processor is configured to:
  detect a sleep state of the first user by reading signals from said first contactless biometric sensor based on at least one of a detected change in the first user's heart rate, body movement, respiration, or presence;
  detect a sleep state of a second user by reading signals from a second contactless biometric sensor, not integrated into the housing, based on at least one of a detected change in the second user's heart rate, body movement, respiration, or presence;
  initiate a first wind-down routine upon detecting a sleep-readiness state of one of the first user or the second user, the first wind-down routine comprising at least one of playing relaxing sounds or playing a respiration entrainment sound; and
  play noise-masking sounds upon detecting that one of the first user or the second user has fallen asleep,
  wherein the processor is configured to play the sounds of the first wind-down routine for the first user and play the noise-masking sounds simultaneously for the second user, and wherein at least one of the noise-masking sounds or the sounds of the first wind-down routine mask the other from being heard by at least one of the first or the second user, wherein the noise-masking sounds mask the first wind-down routine from being heard by the second user, and the sounds of the first wind-down routine mask the noise-masking sounds from being heard by the first user.

2. The sleep assistance device of claim 1, wherein, if the detected sleep-readiness state is of the first user, then the processor is configured to play the sounds of the first wind-down routine using the speaker, and if the detected sleep-readiness state is of the second user, then the processor is configured to play the sounds of the first wind-down routine using earphones in wireless communication with the sleep assistance device.

3. The sleep assistance device of claim 1, wherein the processor is further configured to initiate a second wind-down routine upon detecting a sleep readiness state of the other of the first user or the second user, the second wind-down routine comprising at least one of playing relaxing sounds or playing a respiration entrainment sound.

4. The sleep assistance device of claim 3, wherein the sounds of the second wind-down routine are played over a different output than the sounds of the first wind-down routine.

5. The sleep assistance device of claim 1, wherein the processor is configured to:

play the sounds of the first wind-down routine using one of the speaker or earphones in wireless communication with the sleep assistance device, and play the noise-masking sounds using the other of the speaker or the earphones.

6. A sleep assistance device comprising:

a housing;

a first contactless biometric sensor, integrated into the housing, for determining at least one of a heart rate, a respiratory rate, a presence, or movement of a first user;

a processor; and memory;

wherein said processor is configured to:

detect a sleep state of the first user by reading signals from said first contactless biometric sensor based on at least one of a detected change in the first user's heart rate, body movement, respiration, or presence;

initiate a first wind-down routine upon detecting a sleep-readiness state of the first user, the first wind-down routine comprising controlling earphones in wireless communication with the sleep assistance device to play at least one of relaxing sounds or a respiration entrainment sound, wherein the processor is configured to play the sounds of the first wind-down routine for the first user and play the noise-masking sounds simultaneously for a second user, and wherein at least one of the noise-masking sounds or the sounds of the first wind-down routine mask the other from being heard by at least one of the first or the second user, wherein the noise-masking sounds mask the first wind-down routine from being heard by the second user, and the sounds of the first wind-down routine mask the noise-masking sounds from being heard by the first user.

* * * * *